(12) United States Patent
Kuo et al.

(10) Patent No.: US 11,583,854 B2
(45) Date of Patent: Feb. 21, 2023

(54) HANDHELD LOAC ASSAY DEVICE WITH A NEEDLELESS LIQUID REAGENT DISPENSER

(71) Applicants: Youti Kuo, Penfield, NY (US); Shau-San Wu, New Taipei (TW)

(72) Inventors: Youti Kuo, Penfield, NY (US); Shau-San Wu, New Taipei (TW)

(*) Notice: Subject to any disclaimer, the term of this patent is extended or adjusted under 35 U.S.C. 154(b) by 0 days.

(21) Appl. No.: 16/992,280

(22) Filed: Aug. 13, 2020

(65) Prior Publication Data
US 2022/0072536 A1   Mar. 10, 2022

(51) Int. Cl.
*B01L 3/00* (2006.01)
*G01N 33/487* (2006.01)

(52) U.S. Cl.
CPC .. *B01L 3/502715* (2013.01); *G01N 33/48707* (2013.01); *B01L 2200/16* (2013.01); *B01L 2300/0636* (2013.01); *B01L 2300/0645* (2013.01); *B01L 2400/0433* (2013.01); *B01L 2400/0478* (2013.01)

(58) Field of Classification Search
CPC ............... B01L 3/502715; B01L 3/502; B01L 2200/16; B01L 2300/0636; B01L 2300/0645; B01L 2400/0433; B01L 2400/0478; G01N 33/48707; G01N 27/327
See application file for complete search history.

(56) References Cited

U.S. PATENT DOCUMENTS

2003/0023189 A1*   1/2003   Kuo .................. A61B 10/0045
                                                          600/584

* cited by examiner

*Primary Examiner* — Jennifer Wecker
*Assistant Examiner* — Alea N. Martin

(57) ABSTRACT

A lab-on-a-cartridge (LOAC) handheld assay device including an integrated test cartridge, a carbon nanotube electrode sensor, and a reagent dispenser for dispensing a liquid reagent into the test cartridge. The test cartridge includes a syringe plunger for drawing a test fluid into a test cavity, a bottom wall with a reagent inlet port, and a vibration adaptor for mixing. The reagent input port is attached with a slit valve for engaging with a slit spout of the reagent dispenser as a needleless dispensing system. Carbon nanotube sensors of different three-electrode configurations are provided for testing a volume of test fluid to increase the electrochemical reaction sensitivity. The assay device can be used with a CNT three-electrode sensor for saliva testing for determining glucose concentration.

10 Claims, 13 Drawing Sheets

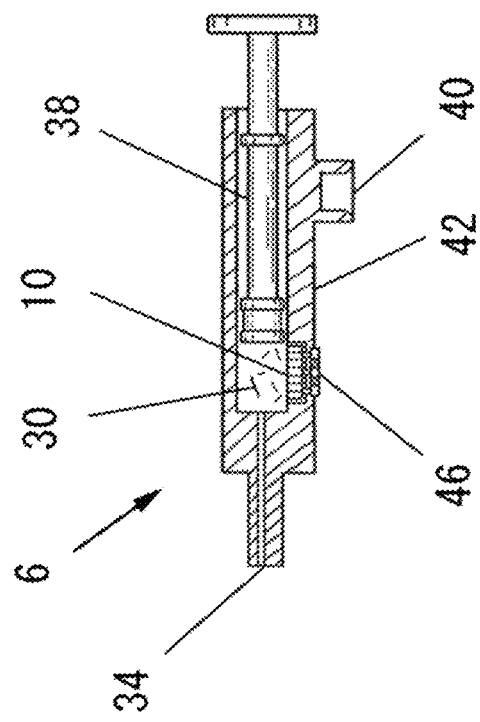
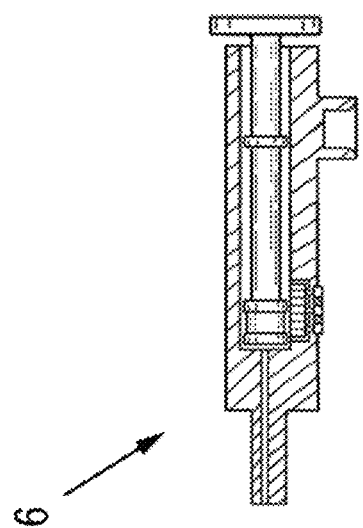
FIG. 2b
FIG. 2a

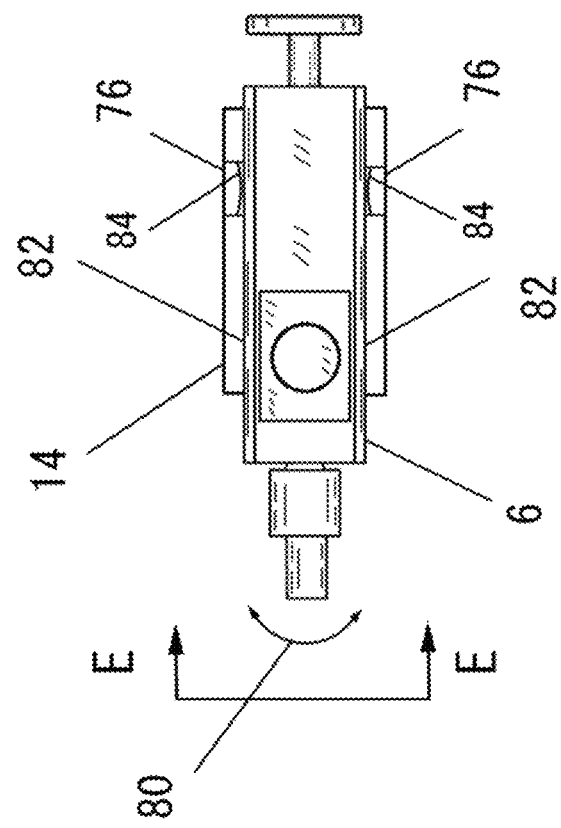
FIG. 3
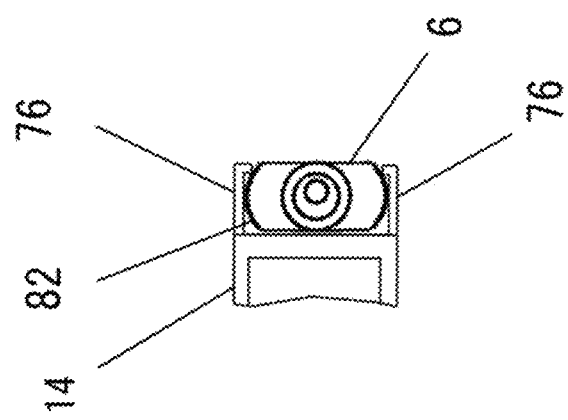
E – E View

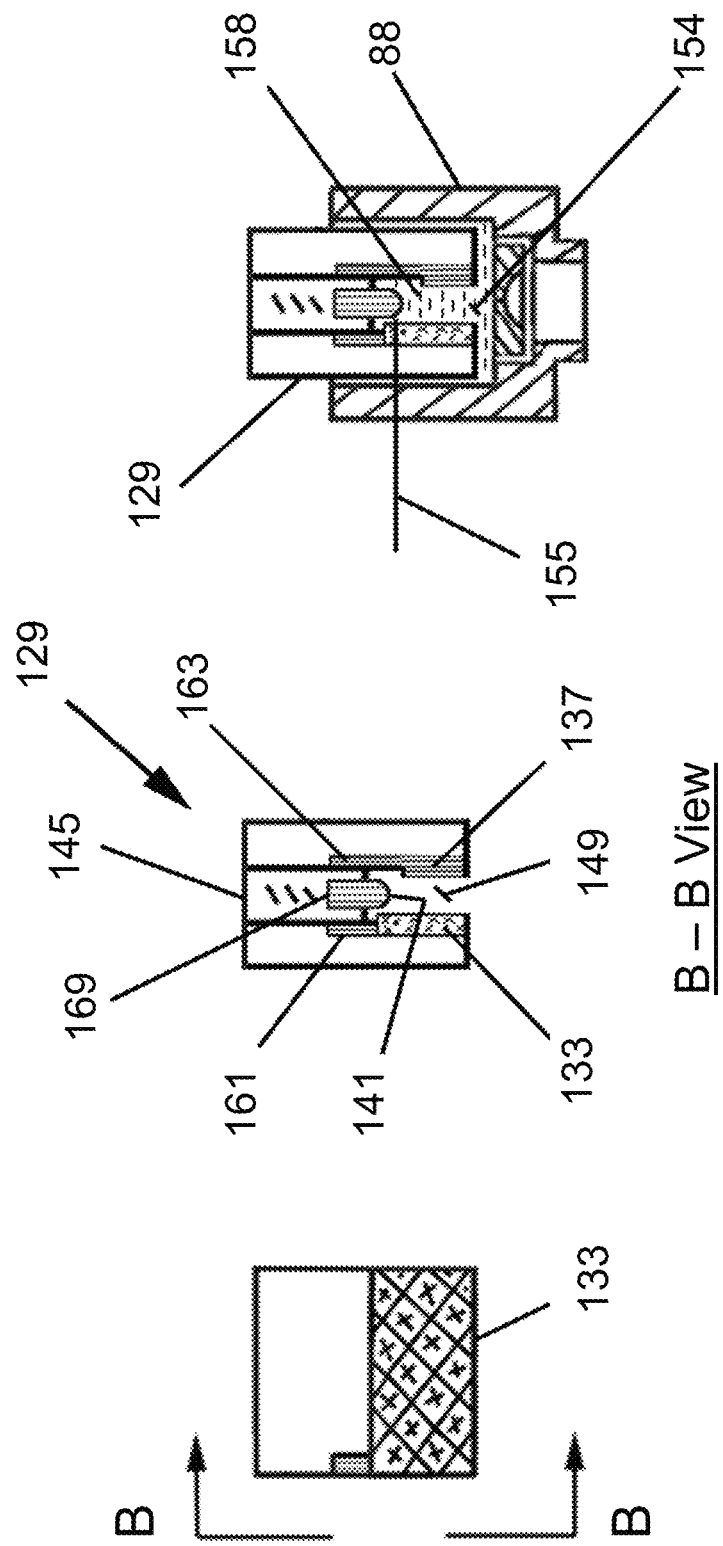

A–A View

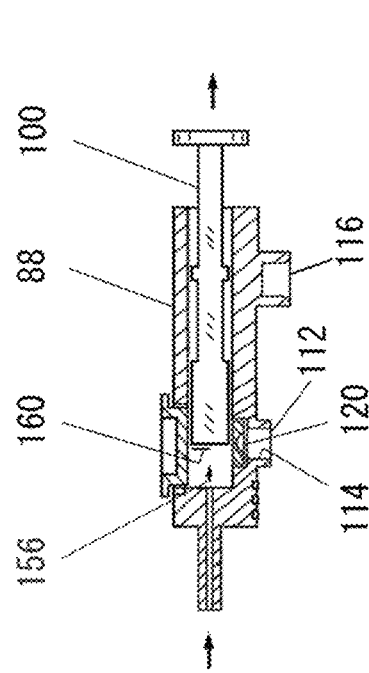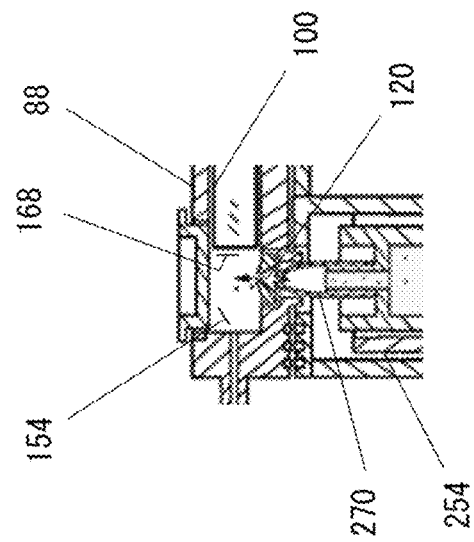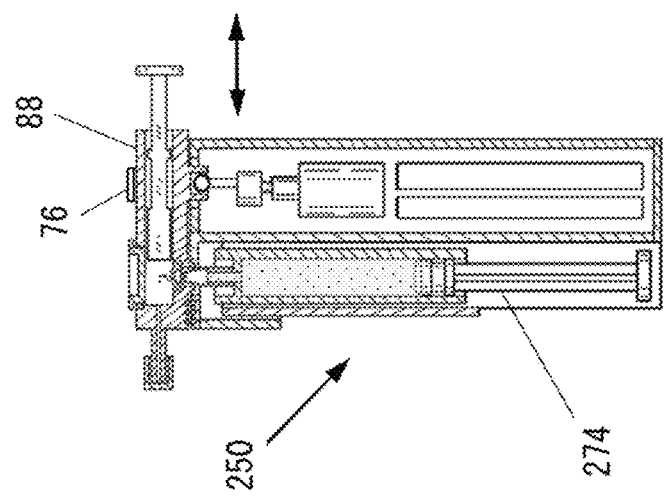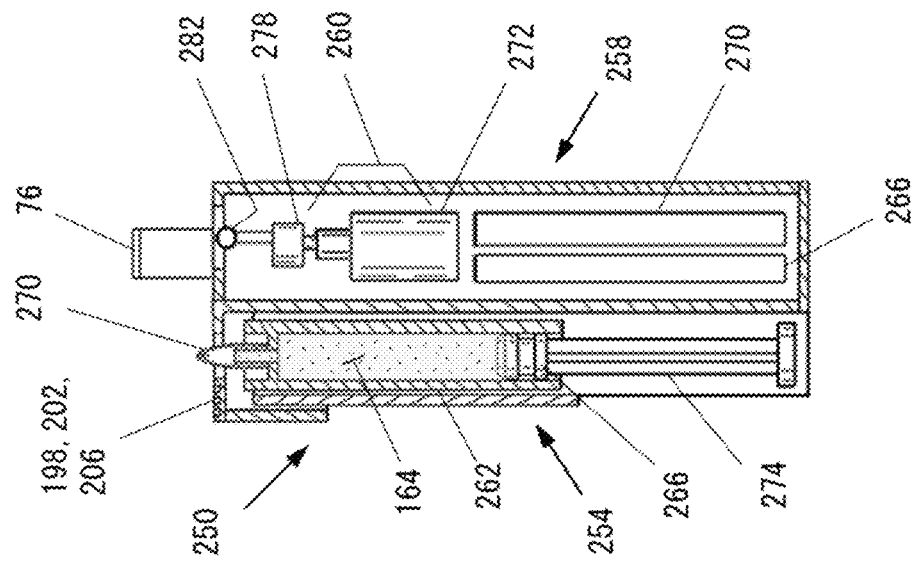

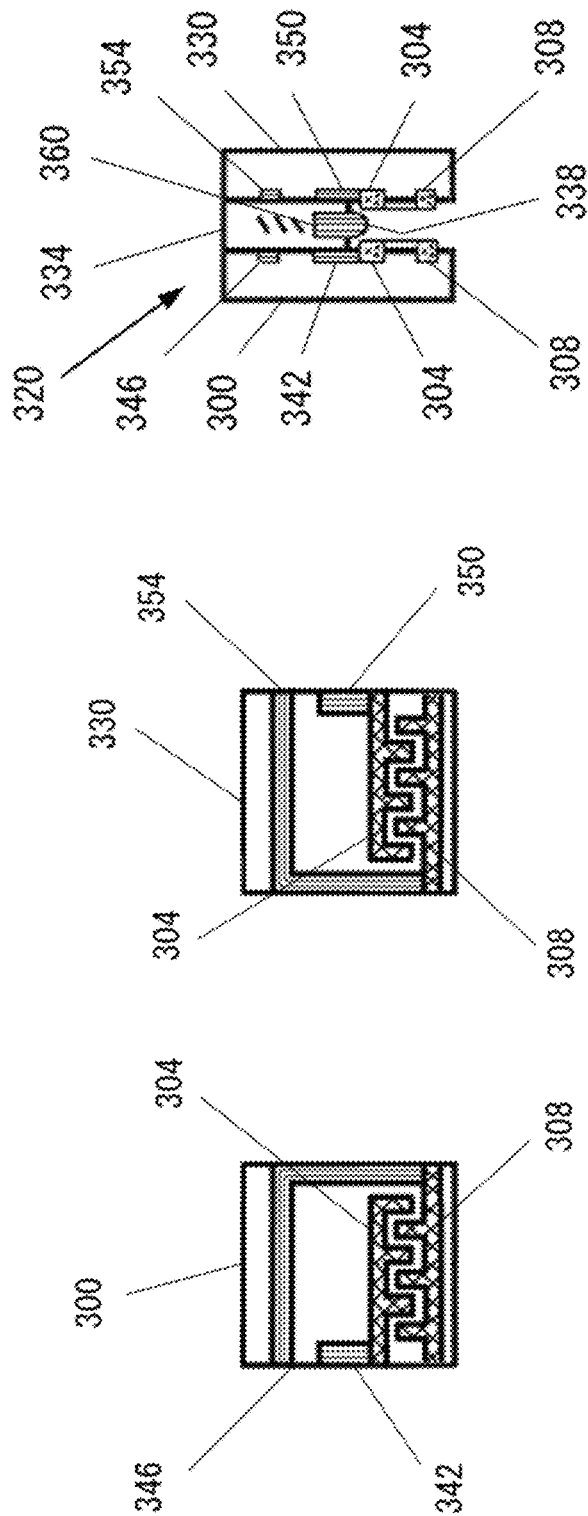

HANDHELD LOAC ASSAY DEVICE WITH A NEEDLELESS LIQUID REAGENT DISPENSER

Continuation of the Provisional Patent Application No. 62/887,367 (filed on Aug. 15, 2019)

BACKGROUND

There is a growing need for home monitoring and diagnosis of body fluids for the early detection of health problems and for reducing health care costs. A handheld diagnostic device is desirable for collecting body fluids into a test cavity for point-of-care testing with a self-contained sensor and a microprocessor for diagnosis. It is desirable for such a handheld diagnostic device to dispense a liquid reagent into the test cavity to broaden the range of tests and the dispensing system is needleless for the safety of the users in non-clinical settings and in home use.

Lab-on-a-chip technology has been under intensive development for its advantage of self-contained test package, faster reaction time, and less disposal of materials. In Lab-on-a-chip, biosensors are integrated in a microfluidic system. The microfluidic system is composed of a cartridge integrating fluidic channels and reservoirs of reagents. The chemical reactions are carried out on a miniature scale. Evaporation of pre-loaded liquid reagents on the chip, however, present reliability problem as it alters the concentration of the reagents in test sample and affects the chemical reactions. Tests in a Lab-on-a-chip device depend mainly on the contact layer of a fluid sample on a biosenser surface, not on the reaction of the whole volume of the fluid sample with the biosensor. There is no vibration for mixing of the fluid sample with a reagent involved as in a laboratory assay. Therefore, the Lab-on-a-chip technology is a very limited pathway for bringing a mature laboratory assay for commercialization.

An alternative to the lab-on-a-chip technology is a lab-on-a-cartridge system that dispenses a liquid reagent on demand into a test cartridge and uses the whole volume of a test fluid for testing to increase the signal intensity. Conventionally, in a clinical laboratory setting, it often requires an apparatus to dispense a measured volume of a liquid reagent from a reservoir to a receiving container. Typically a syringe needle is used to penetrate through a rubber septum of the receiving container to inject the liquid reagent from the reservoir to the receiving container. Before and after the injection both the rubber septum and the needle are sterilized by swabbing with alcohol. However, in home setting a medical monitoring device should not be designed to employ a syringe needle as a syringe needle is a controlled device to prevent drug abuse. Use of a syringe needle is often associated with injecting into the bloodstream and causes serious and sometimes lethal infections. Reuse of needles and syringes are prohibited as it can cause spread of diseases among intravenous drug users even though the syringe and needle are only used by a single person. Besides, a syringe needle is not safe for handling by non-clinical users. For all these reasons, a lab-on-a-cartridge (LOAC) assay device for home use should employ a needleless dispensing system for dispensing a liquid reagent for testing.

Furthermore, most of current lab-on-a-chip devices deal with blood sample, not saliva samples. Saliva is a test fluid of future due to its non-invasive sample collection and its increases signal sensitivity in sensor development for diagnosis. Saliva detection of HIV has been commercialized with home test kit OraQuick brand name marketed by OraSure Technologies. The test uses swab swiping upper and lower gums for saliva sample. However, partly due to small swab sample clinical studies by untrained consumers showed that the OraQuick test will produce about one false negative result out of every 12 tests performed in HIV infected individuals. Also, such test needs to be re-tested on a regular basis. To improve the HIV home test, a convenient device takes a larger saliva sample and provides low cost per test in more frequent basis is desirable.

There are recent advancements in detecting glucose and Alzheimers disease using saliva samples. As described in the Prior Art section that a highly sensitive glucose sensor consisting three electrodes of depositing layers of polymers, metallic nanoparticles, and glucose oxidase enzyme can detect glucose levels at least down to 5 ppm. Also using a saliva sample, a method has been developed in US 20140057364 by Kim et al. to diagnose Alzheimer's disease by using magnetic particles coated with antibodies specifically bonded with beta-amyloid to bond the beta-amyloid contained in the saliva and using a fluorescent detection method to quantify a concentration of the beta-amyloid contained in the saliva. All the above examples of saliva testing in addressing top health concerns indicate the importance of using saliva samples to replace blood samples for non-invasive diagnosis and an urgent need to develop point-of-care devices for saliva assays. To increase the signal sensitivity it is desirable to use a volume of saliva sample to increase the contact of the analyte contained in the sample with a biosensor. Currently, a conventional lab-on-a-chip test device does not address the need of active mixing a volume of test fluid with a reagent, particular a liquid reagent.

In view of many technological barriers in lab-on-a-chip development, in which reagents are pre-loaded in microfluid channels, there is a need to dispense liquid reagents into a test cartridge externally on demand from a compact dispenser which can be used repeatedly for a number of disposable biosensor or test cartridges for the same kind of diagnosis for point-of-care settings such as in hospital, clinic, doctor office and drug stores. The present invention describes a lab-in-a-cartridge (LOAC) assay device that dispenses liquid reagent into an integrated test cartridge having a biosensor for diagnostic testing and the assay device is applicable to testing saliva samples.

(1) Field of the Invention

The present invention relates to a handheld assay device comprising an integrated test cartridge with disposable biosensor, a needleless reagent dispenser and a vibrator for mixing a test fluid with a liquid reagent for point-of-care applications.

(2) Related Prior Art

U.S. Pat. No. 10,732,139 by Zhang et al. describes a saliva glucose monitoring system using an electrochemical method. The sensor contains three electrodes: a working electrode, a counter electrode, and a reference electrode. Among other coating materials glucose oxidase is attached to a component of the working electrode for measuring the amount of glucose present via an amperometric method. The saliva volume can be in the range from a few nanoliters to several milliliters or more. This invention shows the feasibility of using saliva sample for monitoring glucose. However, its working electrode is pre-coated with the reagent material (glucose oxidase enzyme) and the saliva sensor configuration is for testing a layer of saliva sample, not for testing a volume of saliva fluid, therefore, its signal sensitivity is limited.

US Patent Application No. 20140072960 by Lansing provides a self diagnostic test package for collecting and analyzing biological specimens on-site. The test package has one or more openings that allow reagent capsules to be inserted into a testing chamber. A button mechanism allows the reagents to enter the testing chamber and a swab containing the specimen is inserted into the testing chamber to mix with the liquid reagents. A test strip attached to the testing chamber provides chemical reaction with the mixture to test for the presence of an infectious disease. The test package indicates that it is desirable to use liquid reagents for direct mixing with a test fluid. However, the self-contained screening package is limited for testing a swab of sample such as a throat swab, not for a continuum of test fluid.

U.S. Pat. No. 10,274,451 by Kim et al. describes a three-electrode sensor for detecting environmental contaminants. The disposable sensor has a sample chamber to admit a liquid sample. The sensor includes a substrate disposed within the sample chamber that includes at least one conditioning reagent to condition the sample for electrochemical analysis. The sensor unit is an enclosure containing a reagent substrate for reacting with a liquid sample. It is not for use for entering a liquid reagent externally for mixing with a test fluid for electro chemical reaction.

US Patent Application No. 20190185632 by Christy discloses a method of making carbon nanotube film structure. The manufacturing process includes the steps of dispersing carbon nanotubes and polymer into a solvent using high power sonication, applying the suspension of carbon nanotubes onto a continuous, moving, carrier material, and evaporating the solvent from the applied CNT suspension to form a CNT/polymer film over the carrier material. The disclosed method can be applied to coat a reagent layer on a CNT electrode of film configuration.

U.S. Pat. No. 6,132,395 by Landau, et al. provides needleless syringe with prefilled cartridge. The assembly includes: (1) a cartridge having a plunger with a displaceable outlet valve, which is formed of resilient material with at least one flow channel; (2) a nozzle with an injection orifice to receive the outlet valve with fluid access; and (3) a seal disposed between the cartridge and the nozzle preventing fluid leakage. Although the outlet valve is flexible and displaceable for injection, it has an aperture which is not self closing after injection. The outlet valve mechanism is too complex to be used in home setting.

U.S. Pat. No. 8,740,490 by Kuo describes a Dentifrice dispensing electrical toothbrush with integrated dispensing platform and self sealing spout. The dispensing platform contains a flow channel and a self-sealing spout to prevent drying of the dentifrice material at the spout. A slit spout is made of thermoplastic elastomer material for resiliency by dip or injection molding and the cross slits are formed by slicing action of a sharp blade. The slit-spout has multiple flappers forming a normally closed dome-shaped surface when the cavity is empty or not under pressure. The slit spout is used with a pump button for dispensing viscous toothpaste material. It is forced to close by a vacuum force created by releasing the pump button from a depressed position. The slit spout material and configuration is applicable to dispensing liquid without using a pump button due to low viscosity of the liquid.

It is an objective of the present invention to provide a lab-on-a-cartridge (LOAC) diagnostic device using an integrated test cartridge with external reagent input with a needleless dispensing system to mix with a test fluid drawn in a test cavity with vibration. It is another objective to provide three-electrode nanotube sensors for testing a volume of test fluid to increase signal sensitivity for electrochemical reaction. It is a further objective to provide a handheld assay device having a three-electrode nanotube electrode sensor to detect glucose concentration in a saliva sample.

SUMMARY OF THE INVENTION

A lab-on-a-cartridge (LOAC) handheld assay device of the present invention includes an integrated test cartridge containing a test fluid, a liquid reagent dispenser having a self-closing spout delivering a reagent on demand into the test cartridge, and a detection station for measuring the electrochemical reaction between the test fluid and the liquid reagent. The integrated test cartridge includes a sample probe, a test cavity, a syringe plunger for collecting a test fluid, a basewall having a reagent port, and a vibration adaptor for facilitating mixing of the test fluid with the reagent. The reagent port includes a resilient slit valve as an inlet for mating with the self-closing spout of the reagent dispenser. The reagent dispenser consists of a reagent cartridge containing a piston and a self-closing spout, which engages with the reagent port with snug-fit.

Four CNT sensors of three-electrode configurations are provided. The first configuration uses a working electrode of CNT conductive film and a counter electrode substrate with the liquid reagent dispensed into the gap between the electrodes. The second configuration uses CNT conductive films for both working and counter electrodes. The third configuration is a dual-unit CNT sensor, each unit uses etched working and counter electrodes with the liquid reagent dispensed into the gap. The fourth configuration uses a full CNT film coated with a reagent layer as the working electrode and a bare counter electrode substrate for containing a volume of test fluid without using a liquid reagent. All four involves a reference electrode built in the sensors in contact with the test fluid.

In operation, in using the liquid reagent dispenser, the test cartridge is first detached from the detection station. With the plunger at the home position where the test cavity is closed, the inlet probe is placed in a pool of the test fluid and then the plunger is pulled away from the home position to a first predetermined position. The first pulling action draws a fixed quantity of the test fluid into the test cavity. With the inlet probe closed, mounting the test cartridge on top of the reagent dispenser enables the electrical contacts and engages the reagent port and the vibration adaptor with the self-closing spout and the vibrator respectively. Next, pull the plunger further away to a second predetermined position. The second pulling action draws a fixed quantity of liquid reagent from the reagent dispenser into the test cavity. The self-closing spout of the dispenser closes upon the stop of the plunger pulling action. At the same time, the vibrator is activated to impart vibration to the test cartridge to facilitate the mixing of the test fluid with the liquid reagent. After a predetermined time, the result of the electrochemical reaction is indicated in the detector station. Alternatively, the liquid reagent can be injected with a metering motor to drive the dispenser.

BRIEF DESCRIPTION OF THE DRAWINGS

FIG. 2a is a front cross-section view of an integrated test cartridge with a syringe plunger at the home position with the test cavity closed by the plunger.

FIG. 2b is the test cartridge of FIG. 2a with the plunger at an open position.

FIG. 3 is a top view of the test cartridge pivoted by a pair of vibration support arms extended from the detection station.

FIG. 4b is an explosive view of the test cartridge of FIG. 4a.

FIG. 5a is a front view of a CNT working electrode of a three-electrode CNT sensor.

FIG. 5b is a side view of the three-electrode CNT electrode sensor with the working electrode shown in FIG. 5a.

FIG. 5c shows the three-electrode CNT electrode sensor inserted in a test cartridge shown in FIG. 4a.

FIG. 6a is a front view of a CNT electrode film of a three-electrode sensor.

FIG. 6b shows a side view of the three-electrode sensor of FIG. 6a having CNT films for both working and counter electrodes.

FIG. 6c shows the CNT electrode sensor of FIG. 6b inserted in a test cartridge shown in FIG. 4a.

FIG. 8a is a front cross-section view of a device handle including a reagent dispenser and a detection station.

FIG. 8b shows the integrated test cartridge of FIG. 4b having the test cavity partially filled with a test fluid.

FIG. 8c shows the mounting of the integrated test cartridge of FIG. 7b with the test cavity filled with the liquid reagent.

FIG. 8d shows an enlarged view of the test cavity of FIG. 7c with the reagent port opened by the entering reagent flow.

FIG. 9b shows the test cavity of the test cartridge of FIG. 8a.

FIG. 10a is a front view of a first etched CNT electrodes sensor.

FIG. 10b is a front view of a second etched CNT electrodes sensor.

FIG. 10c is a side view of a dual-unit of the etched CNT electrodes sensor.

FIG. 11b shows the test cavity of the test cartridge of FIG. 10a.

FIG. 13c shows the test cavity mounted with the three-electrode sensor of FIG. 12a.

DETAILED DESCRIPTION OF THE INVENTION

Figure 1B:
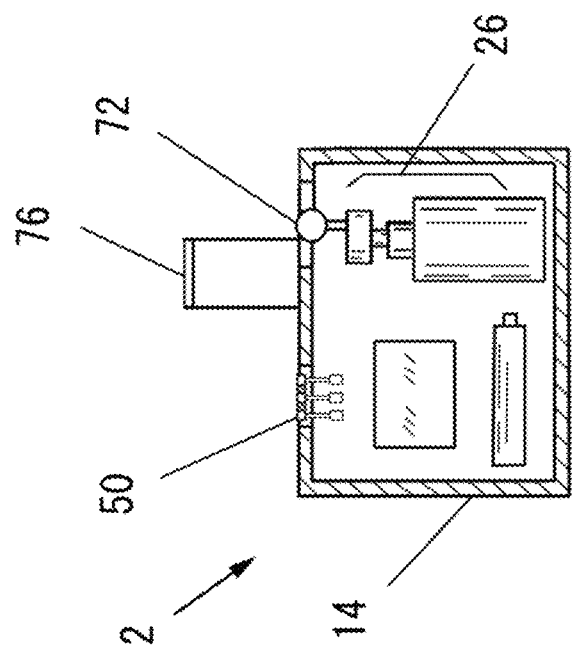
FIG. 1b is the detection station of FIG. 1a without a test cartridge mounted.

Throughout the following detailed descriptions, same reference numerals refer to the same elements in all figures and CNT refers to carbon nanotube.

Integrated Test Cartridge

Figure 1A:
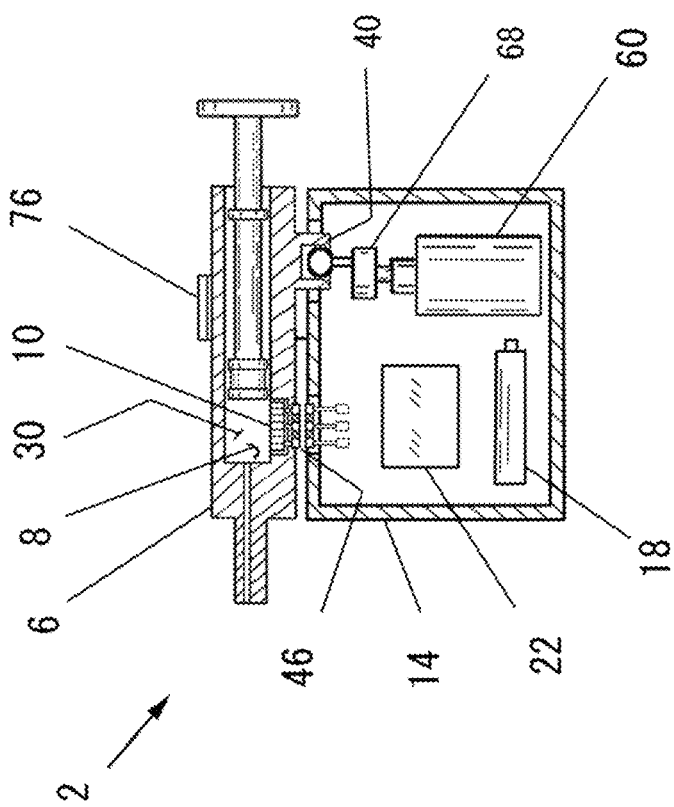
FIG. 1a is a front cross-section view of a handheld assay device showing a detection station having a vibrator mounted with a test cartridge.

A handheld assay device of the present invention is a lab-on-a-cartridge (LOAC) that uses a biosensor including an immobilized reagent or a biosensor that is immersed in a liquid reagent for reacting with a test fluid for detecting a targeted analyte. As shown in FIG. 1a and FIG. 1b, a handheld lab-on-a-cartridge (LOAC) assay device 2 comprises an integrated test cartridge 6 including sensor 10, and detection station 14 including power source 18, control system 22 and vibrator 26. Test cartridge 6 is used to collect test fluid 8 directly and then mounted on the detection station 14 for imparting vibration on the test cartridge and for measuring the reaction signal resulting from the reaction between the biosensor and the test fluid. The detection station includes power source, electrical circuitry, microprocessor and software for analyzing the measured reaction and determining the analyte concentration of the test fluid. FIG. 1b shows the detection station without the test cartridge mounted. Referring to FIG. 2a and FIG. 2b, test cartridge 6 includes test cavity 30, inlet opening 34, syringe plunger 38, biosensor 10 and vibration adaptor 40. FIG. 2a shows the syringe plunger is at the home position, where the test cavity is closed by the syringe plunger at the foremost position against the inlet opening on the front wall. Biosensor 10 is positioned flush with bottom wall 42 not obstructing the movement of plunger 38. The biosensor is electrically connected to electrodes 46 exposed on the bottom side of bottom wall 42. When the test cartridge is mounted on the detection station, electrodes 46 are in contact with electrical interface 50 (shown in FIG. 1b) and vibration adaptor 40 is engaged with vibrator head 72 on the detection station as shown in FIG. 1a. In use, with the test cavity closed and the syringe plunger at the closing position (home position), place the inlet probe in a pool of test fluid and then pull the plunger away from the home position, i.e. away from the inlet opening. Pulling action creates a vacuum force and draws in a quantity of test fluid into the test cavity as shown in FIG. 1b. A marking or a stop feature on the test cartridge can be used to indicate a predetermined amount of test fluid is drawn into the test cavity.

With the test cavity full of the test fluid, the test cartridge is mounted on the detection station for measuring the electrochemical reaction resulting from the interaction of the biosensor with the test fluid. The drive system 26 as shown in FIG. 1b and FIG. 1a includes the motor 60, biased cam 68, and vibratory head 72 for imparting vibration of the test cartridge 6, which has vibration adaptor 40, to facilitate the contact between the test fluid and the biosensor.

Vibrator

FIG. 3 is a top view of test cartridge 6 pivoted by a pair of vibration support arms 76 extended from detection station 14 with each arm having a curved sidewall (contact surface) for guiding pivoting vibration motion of the test cartridge. The vibration of test cartridge 6 is swing motion 80 coupled with lateral back and forth movement with respect to the pivotal positions 84 on sidewalls 82 of test cartridge 6, which are of curved surfaces. The swing motion is constrained by the vibration support arms 76 extending from detection station 14. Each support arm also has curved surface in contact with the curved sidewalls of the cartridge for point contact for the swing motion.

Biosensor

In one embodiment of using the test cartridge of the present invention the sensor can be generally a biosensor or an electrode sensor used with a reagent for electrochemical testing. A biosensor is made up of a transducer immobilized or coated with a biological element that may be an enzyme, an antibody or a nucleic acid. The biological element interacts with the analyte being tested and the biological response is converted into an electrical signal by the transducer. Specifically, a biosensor can be a three-electrodes system that includes one working electrode, a counter electrode, and a reference electrode. For increasing the sensitivity of detection, the working electrode may be coated with single-walled carbon nanotubes (SWNT). Alternatively the working electrode can be made of carbon material deposited with carbon nanotube needles. These carbon nanotubes can amplify the reaction signal with the analyte in the test fluid by providing extremely large effective contact area for electron transfer in the electrochemical system. The electrical current is converted via amperometry to an output voltage for measurement. An example of a biosensor using carbon nanotube electrodes is described in the U.S. Pat. No. 9,244,035 by Zhang, et al. for measuring glucose concentration in saliva. In the saliva testing the nanotube electrode is coated with glucose oxidase enzyme for reacting with the glucose in the saliva sample with the output voltage measured by the detection station to indicate the glucose concentration. In the lab-on-a-cartridge (LOAC) assay device of the present invention, such a biosensor using carbon nanotube (CNT) electrode is inserted in the test cavity holding a volume of test fluid and a liquid reagent, which are mixed vigorously by vibration to increase contacts between the solution and the CNT electrodes. In this lab-on-a-cartridge (LOAC) configuration, the analyte contained in the test fluid has higher frequency of contact with the electrode surfaces to enable faster reaction time and higher signal intensity for measuring electrochemical reaction than that in a conventional lateral flow test.

Liquid Reagent Dispenser

Figure 4A:
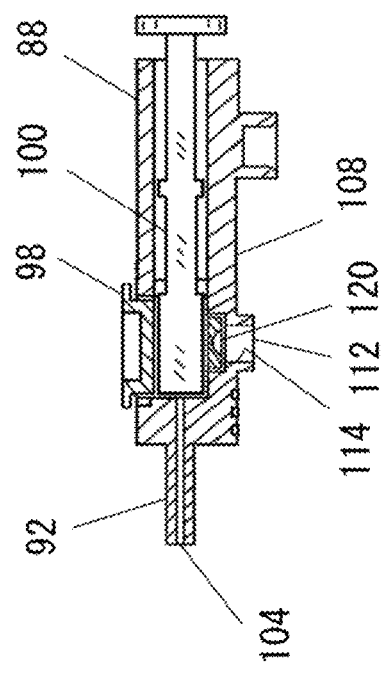
FIG. 4a is a front cross-section view of a test cartridge having a reagent port.
Figure 4B:
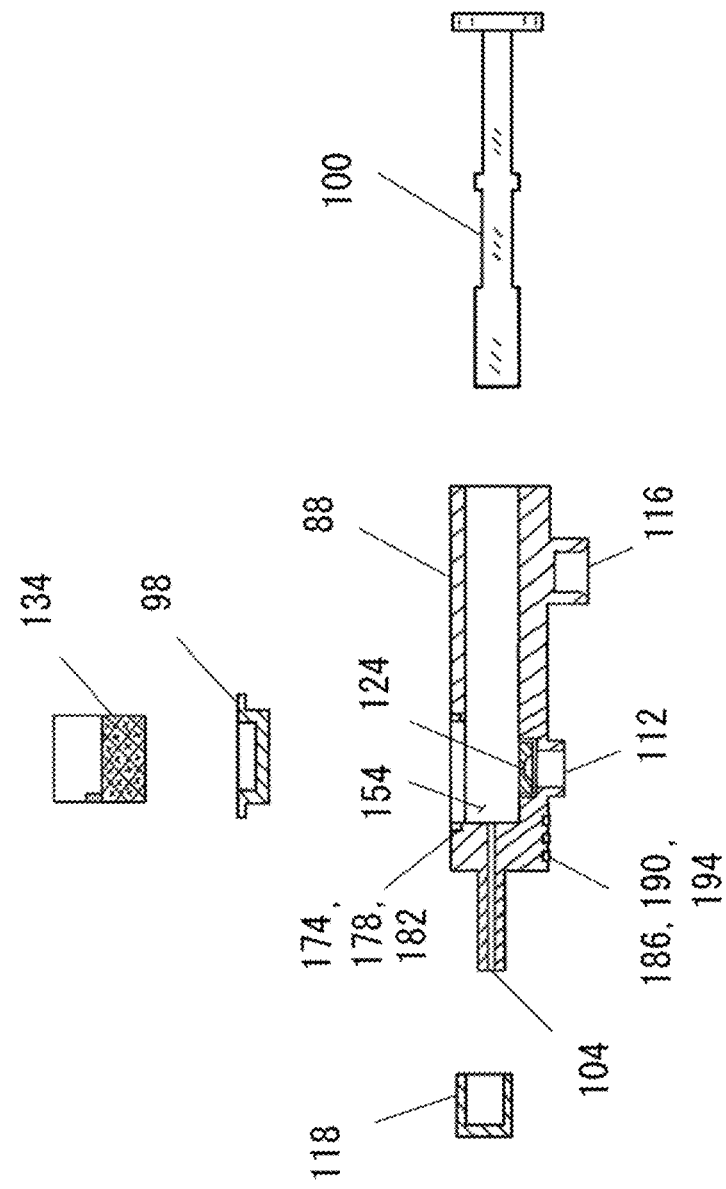

An embodiment of a lab-on-a-cartridge (LOAC) assay device of the present invention is the use of an integrated test cartridge with liquid reagent input to mix with a volume of test fluid to increase the sensitivity of reaction signal for detecting a target analyte. FIG. 4*a* and FIG. 4*b* show an integrated test cartridge, which is to be mounted on an assay device handle including a liquid reagent dispenser shown in FIG. 5*a*, which will be described in latter section. The integrated test cartridge of the present invention is a lab on a cartridge with external reagent input into the test cavity. As shown in FIG. 4*a* and FIG. 4*b*, the integrated test cartridge 88 includes a sample probe 92, a test cavity 154 with lid 98, a syringe plunger 100 for sample collection. The test cavity 154 has a front wall with inlet opening 104 for entering a test fluid and a base wall 108 attached with a reagent port 112 with dispenser spout adaptor 114 for entering a liquid reagent dispensed from a reagent dispenser.

The sample probe has a cap 118 covering inlet opening 104 of the flow channel connected to the entrance of the test cavity. Additionally, the base wall 108 also has a vibration adaptor 116 for engaging with a vibratory head in a detection station to facilitate mixing of the test sample with the liquid reagent. The pulling of the syringe plunger away from the home position, where the test cavity is closed, as shown in FIG. 4*a*, draws the test fluid into the test cavity. Reagent port 112 has internal surface attached with a one-way valve, which is a slit valve 120 having cross slit-cuts forming four flexible flappers. The local area of each slit valve or each flapper has slight convex or dome-shaped surface to function as a one-way valve. The convex surface is similar to an elastomeric slit valve that provides self-sealing capability due to the resiliency of the flexible flapper in returning to its original closed shape when no dispensing fluid pressure is applied. As will be described in a latter section the slit valve is to be inserted with the self-closing spout, shown in FIG. 7*a*, of the reagent dispenser of an assay device. The dispenser spout adaptor 114 is a recess providing snug fit for inserting the self-closing spout to inject liquid reagent into the test cavity without leaking the liquid reagent outside the reagent port. After detaching the test cartridge from the reagent dispenser, any excessive liquid reagent remains inside the recess that can be covered by a plug for safe disposal after testing. Furthermore, the dispenser slit spout can be cleaned or sterilized by swabbing with alcohol. The dispenser spout does not contact the test fluid, therefore, is not contaminated by the test procedures and it can be reengaged and reused for next tests.

Bare Nanotube Electrode Film

The integrated test cartridge having a reagent port is to be inserted with a biosensor that can hold a volume of test fluid in the test cavity. Different configurations of the three-electrode CNT sensor are described in the following sections. A three-electrode sensor includes a working electrode, a counter electrode and a reference electrode.

For amplifying reaction signal a working electrode of the present invention comprises of carbon nanotube film with large reaction surface for contacting with the test fluid and the liquid reagent inside the test cavity. An embodiment of the present invention is the use of a three-electrode sensor having at least a bare nanotube electrode film in an integrated test cartridge.

To test a volume of test fluid, the present invention describes a variety of three-electrode sensor configurations for inserting in a test cartridge for holding a fixed volume of test fluid for testing. A three-electrode sensor comprises a working electrode, a counter electrode and a reference electrode.

As shown in FIG. 5*a* and FIG. 5*b*, three-electrode CNT sensor 129 comprises one CNT electrode film as working electrode 134, counter electrode 137, and reference electrode 141. The reference electrode is inserted in insulative spacer 145, which separates the working electrode and the counter electrode. Preferably counter electrode 137 is situated in a substrate or plate opposing CNT working electrode 134 for electrical contact with a test fluid. The counter electrode substrate is inserted with a conductive electrode. Preferably the counter electrode substrate is a CNT film for providing large conductive surface area for performing electrochemical reaction with the CNT working electrode. The spacer separates the working electrode and the counter electrode. The CNT electrode film, the counter electrode and the spacer forms an open channel 149 for holding a volume of test solution (test fluid plus liquid reagent) when sensor 129 is inserted in test cavity 153 in test cartridge 88 as shown in FIG. 5*c*. The electrical terminals 161, 163 of working electrode and counter electrode, respectively, are on the same edge side of sensor 129 as shown in FIG. 5*b*. Additionally, reference electrode 141 is exposed to open channel 149 for contacting a test fluid and its electrical terminal 169 is positioned on the same edge side of the sensor. These electrical terminals are positioned above the test cavity and above the full line 155, shown in FIG. 5*c*, to remain dry not in contact with the test solution when the three-electrode sensor is mounted in a test cartridge. Referring to FIG. 4b and FIG. 5b, terminals 161, 163, 169 of sensor 129 are in contact with the interface electrical contacts 174, 178, 182 (FIG. 4b) on the side wall of the test cavity, which are wired in electrical connections with the electrical terminals 186, 190, 194 (FIG. 4b), respectively, on bottom wall 108 of test cartridge 88. Three electrical terminals 186, 190, 194 are to be in contact with electrical contacts 198, 202, 206 on the interface surface of the assay device handle as will be shown later in FIG. 7c.

With sensor 129 being immersed in test cavity 153 as shown in FIG. 5c, working electrode 133, counter electrode 137 and reference electrode 141 are exposed to the mixture of the test fluid and the liquid reagent to form a three-electrode circuit for measuring electrochemical reaction. The areas of the CNT electrodes are immerged or wetted in the test cavity filled with the test fluid and the liquid reagent to full line 155 as shown in FIG. 5c. Below the full line the electrodes are wetted. Outside the wetted area the CNT electrodes are connected to lead electrodes, which have distal ends forming electrode terminals above wet line 155 to mate with corresponding contacts in the test cartridge.

When a voltage is applied to the circuit, electrical current flows through the gap between the working electrode and the counter electrode. At the same time, the vibrator is activated to impart vibration to the test cartridge to facilitate the mixing of the test fluid with the liquid reagent inside the test cavity. The vibration also promotes the contact between the mixed solutions with the CNT electrodes. After a predetermined time, the result of the electrochemical reaction represented by current and voltage responses (C-V curves in cyclic voltammtry) can be indicated in the detection station. A software algorithm can be used to determine the concentration of targeted specific analyte in the test fluid.

Methods of manufacturing nanotube conductive films are well known in the art. Specifically a means of manufacturing carbon nanotube films is described in US Patent Application No. 20050081983 by Nakayama, et al., which employs a common chemical vapor deposition (CVD) process combined with the use of acetylene gas for producing nanotube bristles. Its method uses an endless CVD belt coated with nanotubes to transfer the nanotubes to a conductive film by pressing the CVD belt at a sharp turn against a conductive film.

Figures 6A, 6B, 6C:
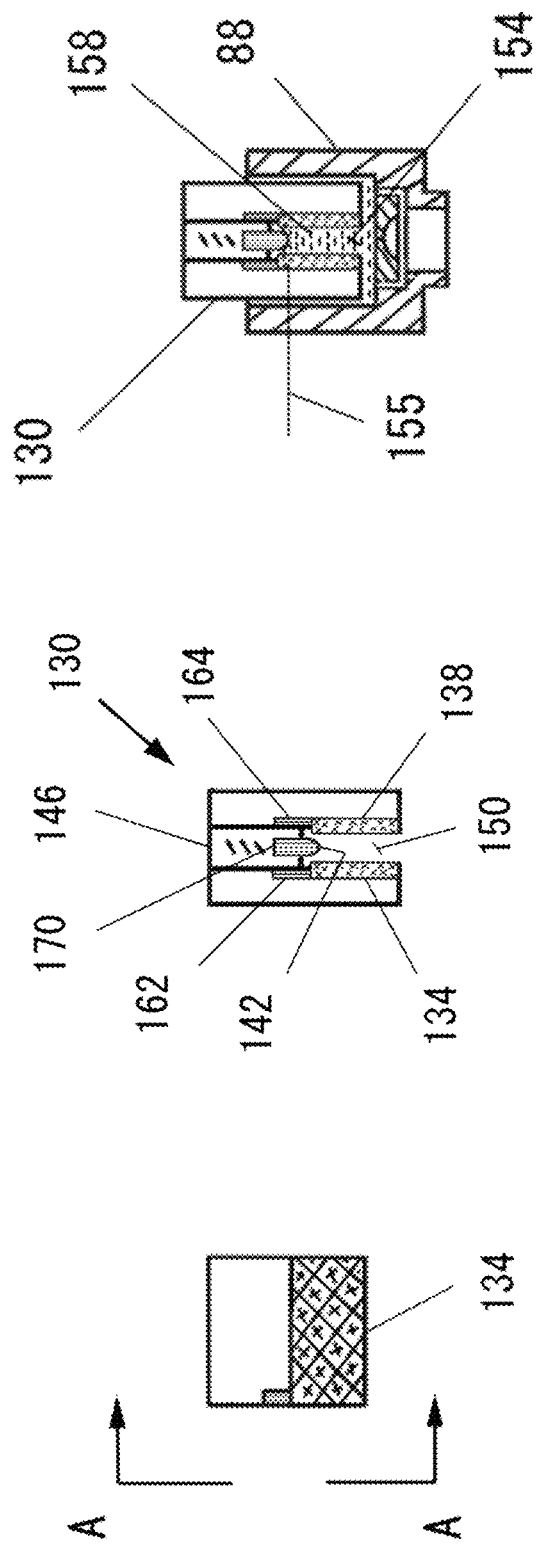

In addition to a working electrode using a CNT film, a CNT film can be used as a counter electrode for increasing detection sensitivity. As shown in FIG. 6a and FIG. 6b, a three-electrode CNT sensor 130 comprises two CNT electrode films, the first film being working electrode 134 and the second film 138 being counter electrode, and a reference electrode 142 inserted in spacer 146. The spacer separates the working electrode and the counter electrode. The two CNT electrode films and the spacer forms an open channel 150 for holding a volume of test solution (test fluid plus liquid reagent) when the sensor 130 is inserted in test cavity 154 in test cartridge 88 as shown in FIG. 6c. The electrical terminals 162, 164 of first electrode film and second electrode film, respectively, are on the same edge side of the sensor as shown in FIG. 6b. Additionally, reference electrode 142 is exposed to the open channel 150 for contacting a test fluid and its electrical terminal 170 is positioned on the same edge side of the sensor. These electrical terminals are positioned above the test cavity and above the full line 155, shown in FIG. 6c, to remain dry not in contact with the test solution when the three-electrode sensor is mounted in a test cartridge. Referring to FIG. 4b and FIG. 6b, terminals 162, 164, 170 of sensor 130 are in contact with the interface electrical contacts 174, 178, 182 (FIG. 4b) on the side wall of the test cavity, which are wired in electrical connections with the electrical terminals 186, 190, 194 (FIG. 4b), respectively, on bottom wall 108 of test cartridge 88. Three electrical terminals 186, 190, 194 are to be in contact with electrical contacts 198, 202, 206 on the interface surface of the assay device handle as will be shown later in FIG. 8c.

With sensor 130 being immersed in test cavity 154 as shown in FIG. 6c, working electrode 134, counter electrode 138 and reference electrode 142 are exposed to the mixture of the test fluid and the liquid reagent to form a three-electrode circuit for measuring electrochemical reaction. The areas of the CNT electrodes are immerged or wetted in the test cavity filled with the test fluid and the liquid reagent to full line 155 as shown in FIG. 6c. Below the full line the electrodes are wetted. Outside the wetted area the CNT electrodes are connected to lead electrodes, which have distal ends forming electrode terminals above wet line 155 to mate with corresponding contacts in the test cartridge.

When a voltage is applied to the circuit, electrical current flows through the gap between the working electrode and the counter electrode. With a test fluid containing an electrolyte, charge transfer and redox reactions occur. The test cavity functions as an electro-chemical capacitor. Generally voltage-current scan can determine concentration of electrolyte in a test fluid.

Test Cartridge Usage Steps

Figure 7A:
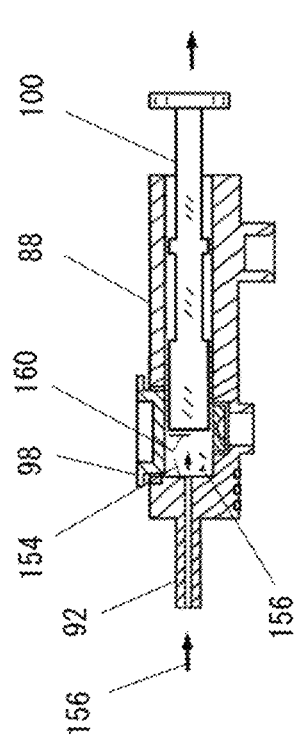
FIG. 7a illustrates the step of entering a test fluid to a test cartridge.
Figure 7B:
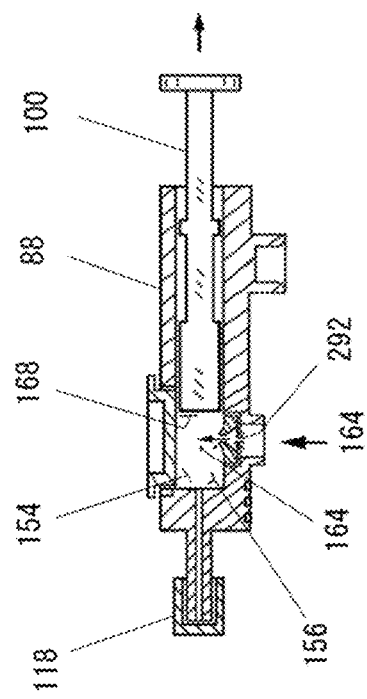
FIG. 7b illustrates the step of entering a reagent fluid to the test cartridge.
Figure 7C:
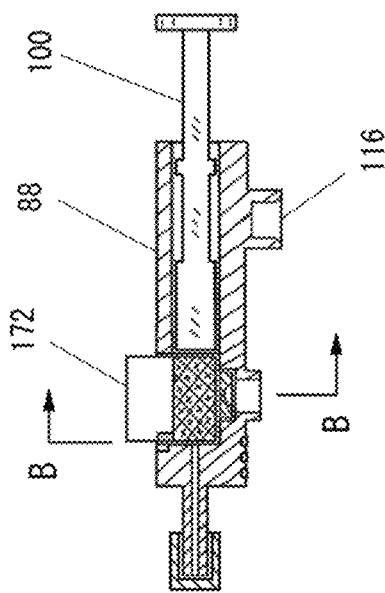
FIG. 7c illustrates the step of inserting a CNT electrode sensor to the test cartridge.

The steps of using the test cartridge of the present invention are described in FIGS. 7a, 7b and 7c. FIG. 7a shows Step 1, the step of entering test fluid 156 to test cartridge 88. Initially with test cavity 154 covered by lid 98, plunger 100 is at the closed position (the home position) expelling the air contained in test cavity 154. The test fluid enters the test cavity by inserting inlet probe 92 into a pool of test fluid, such as under the tongue having a pool of saliva or a tube containing a saliva sample, and then pulling the plunger away from the home position to first predetermined position 160. FIG. 7b shows Step 2, the step of entering liquid reagent 164 into the test cartridge by mounting on a reagent dispenser (to be described in FIG. 8a) and pulling the plunger further away to second predetermined position 168. At the second predetermined position, the unfilled space in the test cavity is reserved for the insertion of a CNT electrode sensor. Optionally, the liquid reagent can be injected into the test cavity manually or by a metering motor that pushes the plunger further away from the home position. FIG. 7c shows Step 3, the step of inserting a CNT electrodes sensor 172 into the test cavity for vibration mixing and measuring the electrical signals of chemical reaction of the test fluid with the liquid reagent. The interactions between the test cartridge and a reagent dispenser are further described in FIGS. 8a, 8b, 8c and 8d.

Needleless Dispensing System

FIG. 8a shows lab-on-a-cartridge device handle 250 of the present invention including a reagent dispenser 254 and detection station 258. It uses a biosensor that is immersed in a liquid reagent injected into the test cavity from the reagent dispenser. The functions of the detection station are similar to that of the detection station as described in FIG. 1a. Reagent dispenser 254 includes reagent cartridge 262 having a tubular wall and piston 266 containing liquid reagent 164, slit-valve spout 270, and syringe plunger 274 for forcing the liquid reagent to exit at the spout to enter a test cavity. Self-closing spout 270 can be made of an elastomeric material or a silicone material having a tubular cap configuration with a cross cut on the dome top to form four elastic flappers. The slit-valve spout has the self-sealing capability to function as a one-way valve. Each flapper has slight convex or dome-shaped surface. The elastic strength of the spout material is sufficient to overcome the viscosity of the liquid reagent for the flexible flappers to return to their original closed shape when no dispensing fluid pressure is applied. In the lab-on-a-cartridge device of the present invention, the self-closing resilient spout is used to replace a conventional needle for injecting a liquid reagent for its safety for point-of-care and home uses by non-clinical users. Detection station 258 in assay device handle 250 is similar to detection station 14 described in FIG. 1*a*. Detection station 258 includes drive system 260, control system 266, and battery 270. The control system includes microprocessor, electrical circuitry and display. The drive system includes motor 272, biased cam 278 and vibratory head 282 for engaging with vibration adaptor 116 of test cartridge 88 (FIG. 8*b*).

In operation, after the first step of filling with the test fluid at first predetermined position 160 as shown in FIG. 8*b*, test cartridge 88 (with the inlet probe closed by the twist cap) is mounted on assay device handle 250 as shown in FIG. 8*c*. As the second step dispenser (syringe) plunger 274 is then moved forward to push liquid reagent 164 and force the slit spout valve 270 open to inject the reagent to test cavity 154 until plunger 100 of the test cartridge being pushed to reach the second predetermined position 168 as shown in FIG. 8*c* and FIG. 8*d*. Optionally, the plunger of the test cartridge can be actively further pulled away to draw in the liquid reagent from the dispenser. The openings of slit valve 120 in the reagent port and dispensing spout 270 in the reagent dispenser are shown in the enlarged view shown in FIG. 8*d*. The amount of reagent required depends on the volume of test fluid in the test cavity for maximizing the reaction signal. Alternatively, the above first step and the second step can be reversed before a CNT electrode sensor is inserted into the test cavity.

Referring to FIG. 8*d*, when test cartridge 88 is mounted on reagent dispenser 254, slit spout 270 is in snug fit inside reagent port 112 with recess adaptor 114. To ensure that the tip of the slit spout not to touch the slit cut, the depth of the recess adaptor 114 from the bottom surface of the test cartridge is greater than the fit-length of the slit spout such that there is a clearance space between the tip of the slit spout and the slit cut. The slit valve and the slit spout are designed not to have any physical contact when the slit spout is docked in the recess adaptor. The slit valve 120 of the reagent port is opened by the pressurized liquid reagent forced into its opening under the dispensing action, which is either by moving the dispenser plunger forward or by pulling the test cartridge plunger away from the home position. This clearance space will be a buffer zone filled with excessive reagent dispensed from the slit spout. This excessive reagent in the buffer zone serves as an insulation fluid to prevent any contact between the test fluid in the test cavity and the surface of the slit spout. At the end of the dispensing action the rebound of the elastic flappers forces the reagent port and the slit spout to close in sealing condition. As the slit spout is isolated from contacting with the test fluid there is no cross-contamination between the test cartridge and the reagent dispenser. The engagement of the slit spout and the slit valve in the reagent port as describe above forms a needleless dispensing system.

Note that the handheld assay device is portable that the whole device can be stored in a home refrigerator for keeping the liquid reagent in low temperatures if required.
Three-Electrode CNT Sensor After filling the test cavity with the test fluid and the liquid reagent, the remaining space in the test cavity allows the insertion of a CNT electrodes sensor for testing to fill up the test cavity. As shown in FIG. 9*a*, the insertion of biosensor 172 engage its electrical terminals 162, 164, 170 with the electrical contacts on the interface wall of the test cartridge, which are in electrical communication with electrical contacts 198, 202, 206 on the assay device handle 250 as shown in FIG. 9*b*.

Figure 9C:
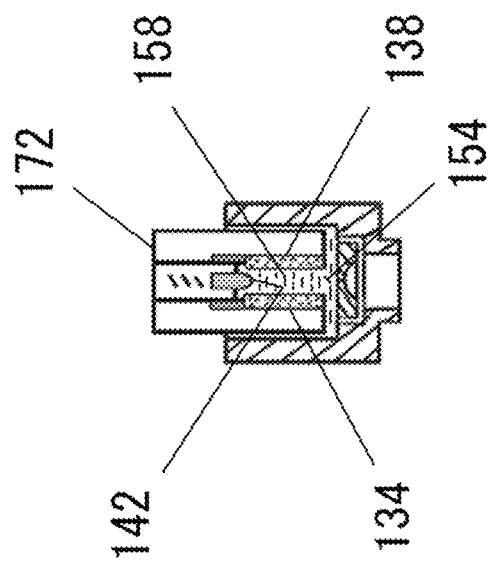
FIG. 9c is the side view of the test cavity showing the electrical terminals of the CNT electrode sensor.
Figure 9B:
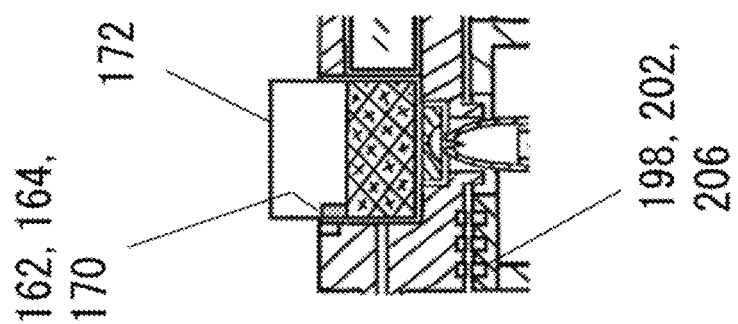
Figure 9A:
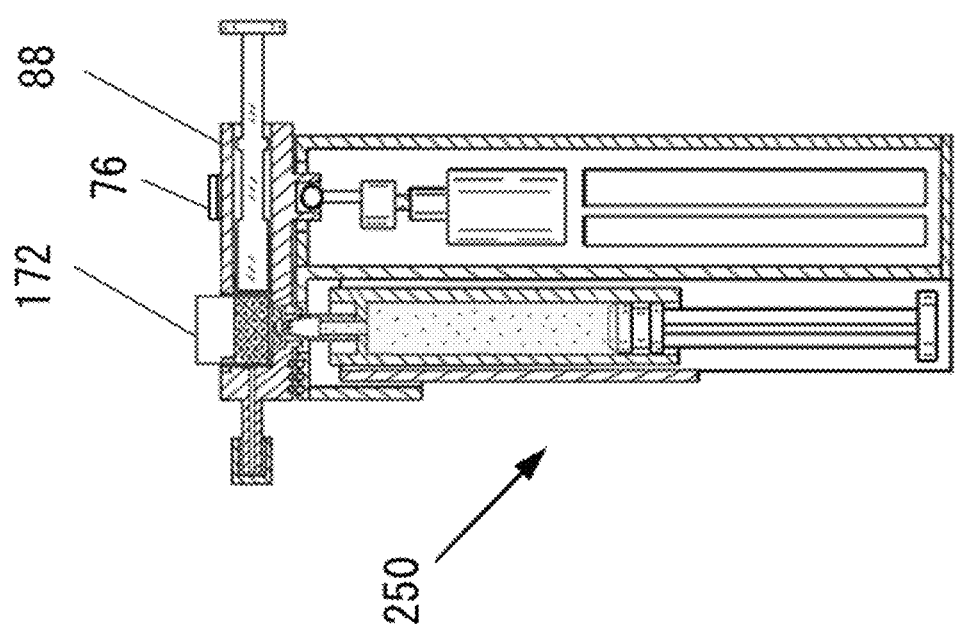
FIG. 9a shows a test cartridge inserted with a CNT electrodes sensor mounted on the reagent dispenser.

With biosensor 172 immersed in test cavity 154 as shown in FIG. 9*c*, working electrode 134, counter electrode 138 and reference electrode 142 are exposed to the mixed solution 158 of the test fluid and the liquid reagent to form a three-electrode circuit for measuring electrochemical reaction. When a voltage is applied to the circuit, electrical current flows through the gap between the working electrode and the counter electrode. At the same time, the vibrator is activated to impart vibration to the test cartridge to facilitate the mixing of the test fluid with the liquid reagent inside the test cavity. The vibration also promotes the contact between the mixed solutions with the CNT electrodes. After a predetermined time, the result of the electrochemical reaction represented by current and voltage responses (C-V curves) can be indicated in the detection station. A software algorithm can be used to determine the concentration of targeted specific analyte in the test fluid.
Dual Etched CNT Electrodes Sensor Alternatively, instead of using CNT electrode films as shown in FIG. 5*a*, 5*b*, 5*c*, an etched CNT electrodes sensor can be used in a test cartridge to increase the sensitivity of detection. FIG. 10*a* shows an etched CNT electrodes sensor 300 having a branch of working electrode fingers 304 and a branch of counter electrode fingers 308. The working electrode fingers and the counter electrode fingers in this etched pattern are equally and closely spaced without touching. The electrode finger width and height are generally over 100 μm and 30 μm, respectively. The spacings or distances between adjacent and juxtaposed working and counter electrode fingers are on the scale of a few hundreds of micrometers range. The small clearances enable high current flow between the working and the counter electrodes to increase the detection sensitivity to the electrochemical reaction of the test fluid and the liquid reagent covering the electrodes.

The fabrication of etched CNT electrodes is known in the art as mentioned in the Prior Art section. A carbon nanotube array is grown on a flat surface of a silicon wafer by using a chemical vapor deposition (CVD) method. The carbon nanotubes are free standing wires grown in a range from about 5 microns to about 50 microns along a direction perpendicular to the flat surface of the silicon wafer. The electrodes pattern can be formed by laser etching, chemical etching, or lithography.

To test a volume of test fluid, two etched CNT electrodes units are used to form a three-electrode sensor for inserting in the test cartridge. As shown in FIG. 10*c*, dual-units CNT-electrodes sensor 320 consists of two etched CNT-electrodes units, with first unit 300 shown in FIG. 10*a* and second unit 330 shown in FIG. 10*b*. The two units are separated by spacer 334, which is inserted with reference electrode 338. The two electrode units and the spacer forms an open channel (gap space) for holding a volume of test solution, which is a mixture of test fluid and liquid reagent, when the sensor is inserted in a test cartridge. The spatial arrangement of the electrodes of second unit 330 is the mirror image of first unit 300 to enable that electrical terminals 342, 346 of the first unit and 350, 354 of the second unit are on the same edge side of the biosensor as shown in FIG. 10c. Additionally, reference electrode 338 is exposed to the test solution and its electrical terminal 360 is positioned on the same edge side of the sensor. These electrical terminals are positioned above the test cavity to remain dry not in contact with the test solution when the electrodes sensor is mounted in a test cartridge. The electrical terminals of the biosensor are in contact with the interface electrical contacts on the side wall of the test cavity, which are wired in electrical connections with the electrical contacts on the bottom wall of the test cartridge.

Dual-Units Etched CNT Electrodes Sensor

Figure 11C:
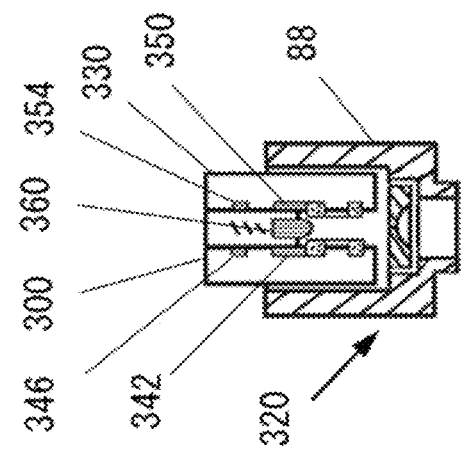
FIG. 11c is the side view of the test cavity mounted with the dual-unit etched CNT electrodes sensor.
Figure 11B:
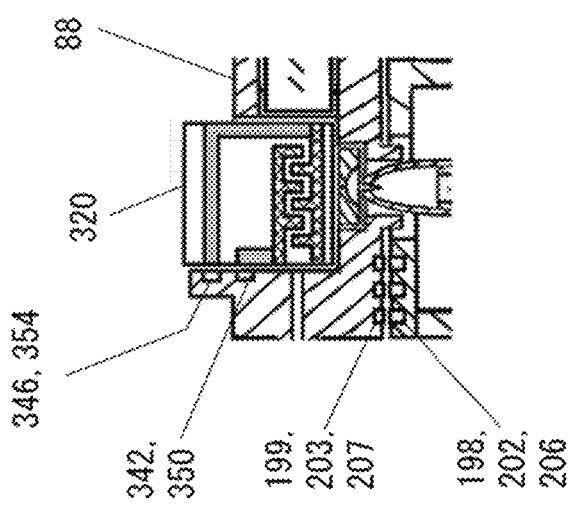
Figure 11A:
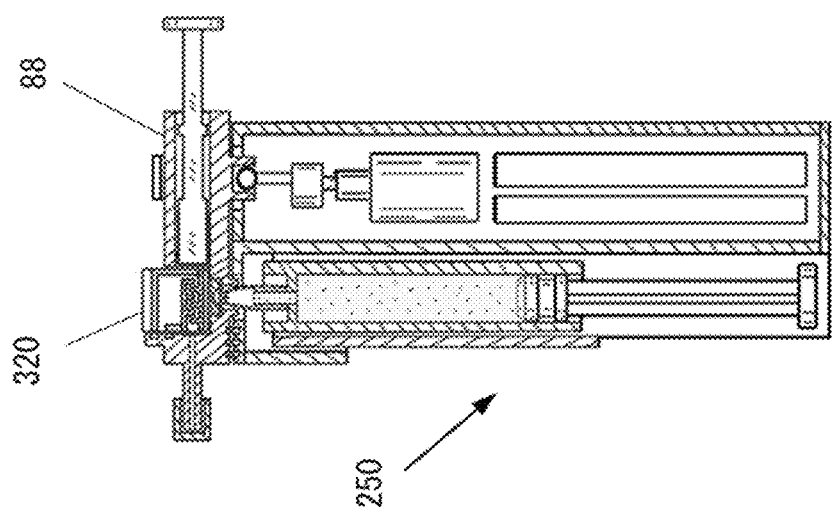
FIG. 11a shows a test cartridge inserted with a dual-unit etched CNT electrodes sensor mounted on a reagent dispenser.

FIG. 11a shows a test cartridge inserted with dual-units etched CNT-electrodes sensor 320 mounted on the assay device handle 250. The electrical contacts 199, 203, 207 on the bottom wall of the test cartridge are in contact with the interface contacts 198, 202, 206 on the assay device, as shown in the enlarged view of the test cavity in FIG. 11b. The interface contacts are in electronic communication with firm ware and the control system of the dispenser and detection device.

With the biosensor being immersed in the test cavity as shown in FIG. 11c, working electrode 304 and counter electrode 308 of first sensor unit 300 and second sensor unit 330, along with common reference electrode 338 are exposed to the test solution to form two separate three-electrodes circuits for measuring electrochemical reaction. When a voltage is applied to each sensor unit circuit, electrical current flows through the gap between the working electrode and the counter electrode of each sensor unit. The electrical signals from the electrochemical reactions of the two units can be separately recorded or averaged for analysis by the signal detection system of the assay device.

Dispensing with a Metering Motor

Figure 12:
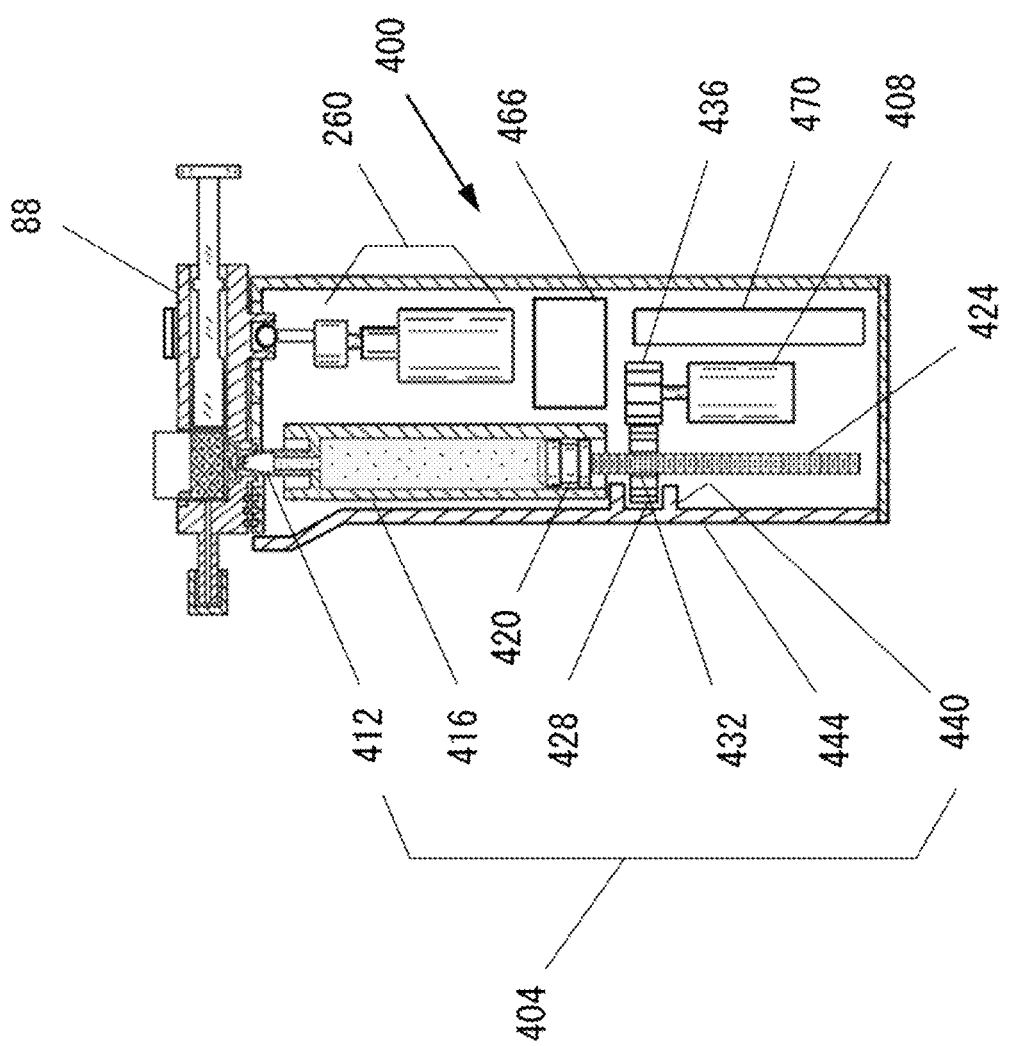
FIG. 12 is a front cross-section view of an assay device having a reagent dispenser driven by a metering motor.

Alternatively, the dispensing of the liquid reagent can be controlled by a stepper motor for metering the amount of reagent into the test cavity. FIG. 12 shows assay device 400 having reagent dispenser 404 driven by a metering motor 408. The dispensing mechanism comprising slit spout 412, syringe barrel 416, piston 420, lead screw 424, and a retaining gear 428 with inner threads 432, drive gear 436 and stepper motor 408. The inner threads of the retaining gear engage with the lead screw. The retaining gear, engaged with the drive gear, is free to rotate between two ribs 440 expended from side frame 444 of the assay device. The rotation of the stepper motor turns the retaining gear to cause the rotation of the lead screw to advance the piston to dispense the liquid reagent. The metering motor is controlled by the operation system of the assay device on the timing and the dosage of the liquid reagent dispensed into the test cavity.

Three-Electrode Sensor with Coated CNT Film

Figure 13C:
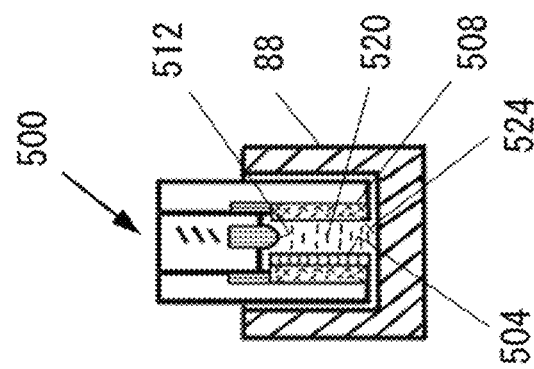
Figure 13B:
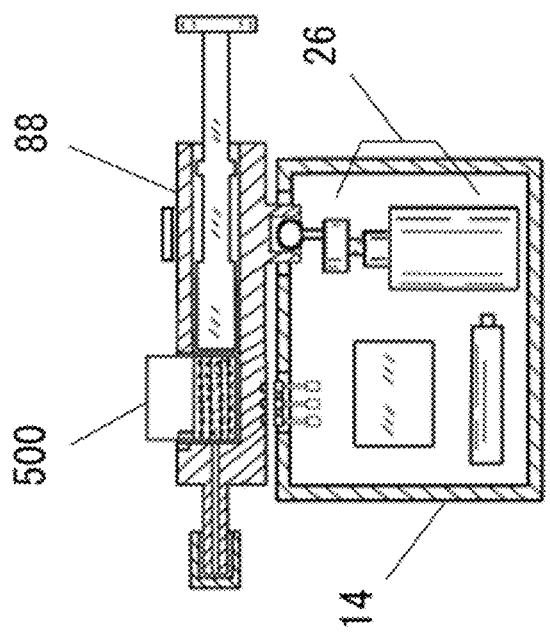
FIG. 13b shows a test cartridge inserted with the three-electrode sensor of FIG. 12a mounted on a detection station.
Figure 13A:
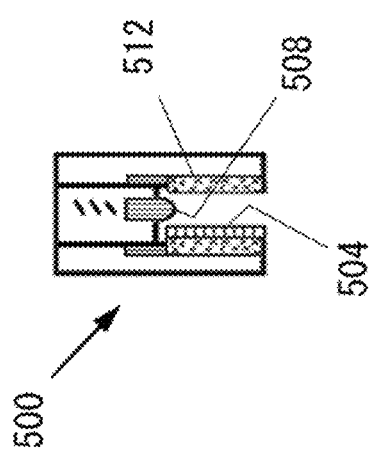
FIG. 13a shows a three-electrode sensor having a CNT electrode film coated with a reagent layer.

Another embodiment of the present invention of the three-electrode sensor configuration is using a reagent-coated CNT electrode as the working electrode without using a liquid reagent. FIG. 13a shows three-electrode sensor 500 having reagent-coated CNT film 504 as the working electrode, bare CNT film 508 as the counter electrode, and reference electrode 512. The fabrication of a reagent-coated CNT film is known in the art. A CNT film can be manufactured by applying a highly dispersed CNT-polymer-solvent suspension mixed using ultrasonication, over a carrier, using a coating process, and drying to form the CNT/polymer film. The fabrication method is described in the US Patent Application No. 20190185632 by Christy. Optionally, a working electrode can be coated with multiple functional layers including a sublayer of chitosan, a sublayer of gold nanoparticles deposited onto the chitosan, and a sublayer of functional reagent material (for example, glucose oxidase for saliva testing) deposited onto the gold nanoparticles. In application a reagent-coated CNT sensor is inserted in a test cartridge without input of liquid reagent. FIG. 13b shows test cartridge 88 inserted with a three-electrode sensor mounted on detection station 14 as shown in FIG. 1a, which does not include a reagent dispenser. Test fluid 520 enters test cavity 524 to fill up the gap, as shown in FIG. c, between reagent-coated working electrode 504 and counter electrode 508 with reference electrode 512 exposed to the test fluid. Such a film configuration has major advantages of large reaction area and narrow gap to enable high current flow between the working electrode and the counter electrode under an applied voltage. Vibrator 26 of detection station 14 imparts vibration of the test cartridge to enable sufficient contact of the volume of the test fluid with the reagent-coated working electrode to increase the efficiency of its electro chemical reaction. For applications, it has been reported in prior art that saliva testing for glucose concentration relies on the contact of a layer of saliva sample on electrodes. To increase the signal sensitivity, the present invention uses a CNT electrode sensor containing a volume of saliva sample for testing. For application, the CNT sensors and the integrated test cartridges of the present invention can be used for saliva testing for glucose concentration. In using a CNT sensor having CNT conductive films for the working and the counter electrodes as shown in FIG. 9c, the test cartridge is entered with a saliva sample and liquid glucose oxidase. For using a dual-unit CNT sensor using etched electrodes as shown in FIG. 11c, both the working electrodes and the counter electrodes are etched and exposed to the liquid glucose oxidase. For using a CNT sensor having a full CNT film coated with glucose oxidase as the working electrode as shown in FIG. 13c, no reagent dispenser is needed.

The present invention has been described in detail with reference to body fluids and preferred embodiments thereof. However, variations and modifications can be implemented within the spirit and scope of this invention. The configurations of the integrated test cartridges as described for a handheld diagnostic device can be applied to any laboratory diagnostic devices for testing body fluids or any pourable fluids. Instead of using a sample probe as described, the inlet opening of the test cavity may be configured to be inserted with a cotton swab containing a test fluid such as saliva. Also, the inlet opening of the test cavity may be attached with a syringe needle for entering a blood sample. The integrated test cartridge may contain a filter at the entrance of the test cavity for purifying test fluid or a test fluid is purified prior to entering the test cavity. Furthermore, the dispenser may be equipped with multiple reagent cartridges for injecting different liquid reagents into an integrated test cartridge for testing a test fluid.

RERERENCES

| Cite No. | Publication Number | Publication Date | Name of Patentee/ Author | Relevant passages (title, pages, lines) |
|---|---|---|---|---|
| 1 | U.S. 20140197042 | Jul. 17, 2014 | Zhang et al. | "Saliva glucose monitoring system" |
| 2 | U.S. 20140072960 | Mar. 13, 2014 | Lansing | "Self diagnostic test" |
| 3 | U.S. Pat. No. 10,274,451 | Apr. 30, 2019 | Kim et al. | "Affordable electrochemical detection of |

-continued

| Cite No. | Publication Number | Publication Date | Name of Patentee/ Author | Relevant passages (title, pages, lines) |
|---|---|---|---|---|
| 4 | U.S. 20190185632 | Jun. 20, 2019 | Christy | environmental contaminants" "Carbon nanotube film structure and method for making" |
| 5 | U.S. Pat. No. 6,132,395 | Oct. 17, 2000 | Landau, et al. | "Needleless syringe with prefilled cartridge" |
| 6 | U.S. Pat. No. 8,740,490 | Jun. 3, 2014 | Kuo | "Dentifrice dispensing electrical toothbrush with integrated dispensing platform and self sealing spout" |

We claim:

1. A handheld assay device comprising
   i. a device handle having support frames,
   ii. a reagent dispenser mounted on said handle including a reagent cartridge containing a liquid reagent, a self-closing spout, and a dispensing means for forcing the liquid reagent to exit at said spout,
   iii. an integrated test cartridge detachably mounted on said handle including a test cavity having an inlet opening, a syringe plunger for withdrawing a test fluid into said test cavity, and a base wall having a reagent port in flow communication with said spout of said reagent dispenser,
   iv. a biosensor inserted in said test cavity in contact with the test fluid and the liquid reagent,
   v. a signal detection station attached to said handle in communication with said biosensor said detection station having a power source and a control system for measuring the reaction of said liquid reagent mixing with said test fluid.

2. The handheld assay device of claim 1, wherein said handle including a vibratory head and said test cartridge having a vibration adaptor for engaging with said vibratory head for imparting vibration of said test cartridge.

3. The handheld assay device of claim 1, wherein said reagent port having a slit valve of elastomeric resilient material, said slit valve having multiple flappers forming a normally closed dome-shaped surface when no dispensing force is applied.

4. The handheld assay device of claim 1, wherein said self-closing spout being a slit valve of elastomeric resilient material, said slit valve having multiple flappers forming a normally closed dome-shaped surface when no dispensing force is applied.

5. The handheld assay device of claim 2, wherein said vibration of the test cartridge is a swing motion constrained by the contacts between curved surfaces of the test cartridge and curved surfaces of vibration support arms extending from said handle.

6. The handheld assay device of claim 1, wherein said test cartridge has a vibration adaptor and said handle includes a vibrator for engaging with said vibration adaptor to impart vibration on said test cartridge.

7. The handheld assay device of claim 1, wherein said plunger in said test cartridge draws in the liquid reagent into said test cavity.

8. The handheld assay device of claim 1, wherein said spout is a self-closing slit valve formed by dome-shaped flexible flappers returning to its original closed shape when no dispensing fluid pressure is applied.

9. The handheld assay device of claim 1, wherein said dispensing means includes a metering motor and a piston attached with a lead screw and the metering motor drives the lead screw and the piston to push the liquid reagent into said test cavity.

10. The handheld assay device of claim 1, wherein said test fluid is saliva and said reagent is glucose oxidase.

* * * * *